W. S. KINSLEY.

MACHINE FOR INTRODUCING KNICKERS INTO FABRICS.

APPLICATION FILED JULY 16, 1919.

Reissued Sept. 16, 1919.

14,724.

4 SHEETS—SHEET 1.

Inventor:
William S. Kinsley,
by Emery, Booth, Varney & Varney Attys.

THE COLUMBIA PLANOGRAPH CO., WASHINGTON, D. C.

W. S. KINSLEY.

MACHINE FOR INTRODUCING KNICKERS INTO FABRICS.

APPLICATION FILED JULY 16, 1919.

Reissued Sept. 16, 1919.

14,724.

4 SHEETS—SHEET 2.

Inventor:
William S. Kinsley,
by Emery, Booth, Varney & Varney Attys

THE COLUMBIA PLANOGRAPH CO., WASHINGTON, D. C.

W. S. KINSLEY.

MACHINE FOR INTRODUCING KNICKERS INTO FABRICS.

APPLICATION FILED JULY 16, 1919.

Reissued Sept. 16, 1919.

14,724.

4 SHEETS—SHEET 3.

Inventor:
William S. Kinsley,
by Emery, Booth, Janney & Varney Attys.

W. S. KINSLEY.
MACHINE FOR INTRODUCING KNICKERS INTO FABRICS.
APPLICATION FILED JULY 16, 1919.
Reissued Sept. 16, 1919.
14,724.
4 SHEETS—SHEET 4.
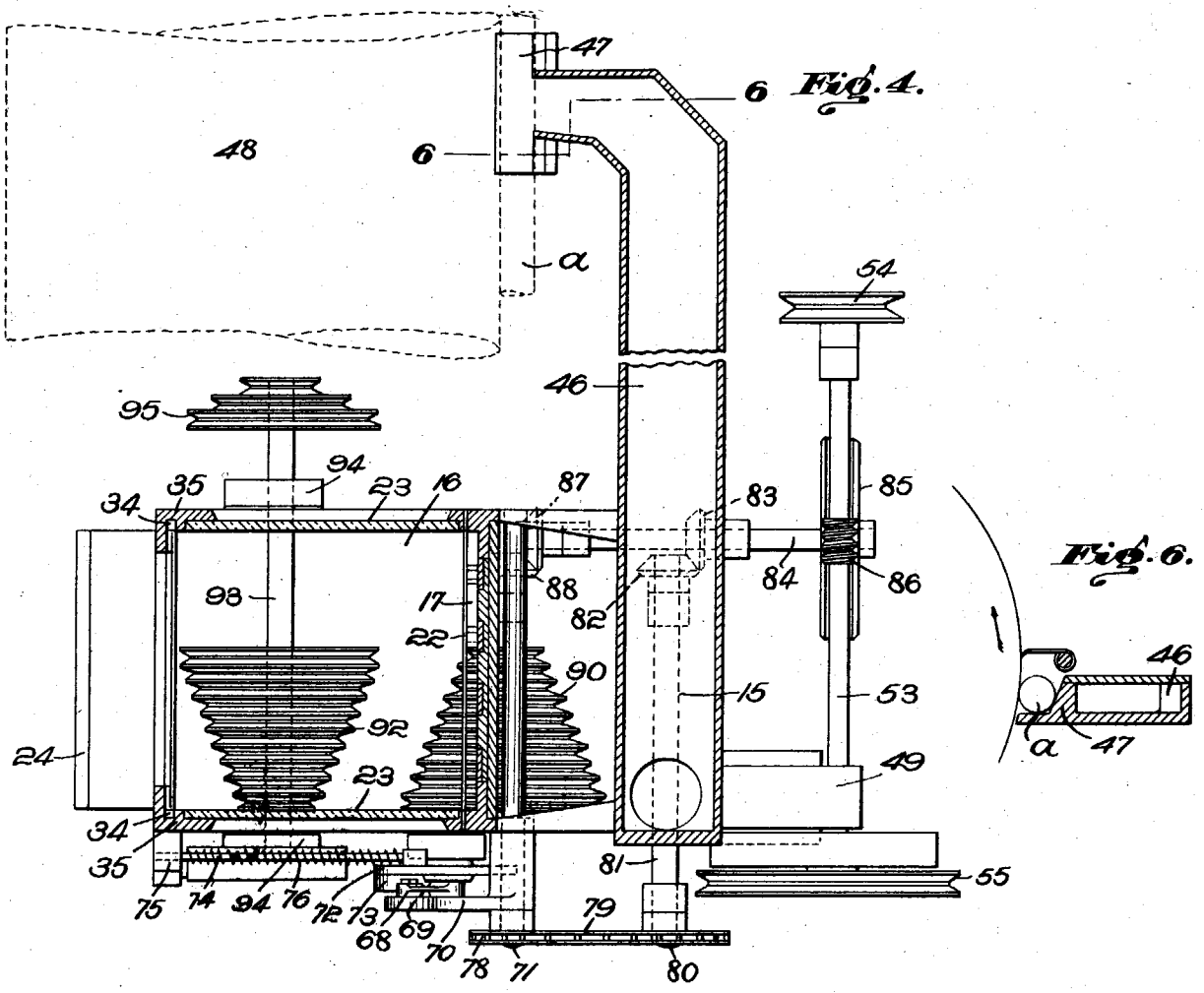
Inventor:
William S. Kinsley,
by Emery, Booth, Janney & Varney
Attys.
THE COLUMBIA PLANOGRAPH CO., WASHINGTON, D. C.

UNITED STATES PATENT OFFICE.

WILLIAM S. KINSLEY, OF READING, MASSACHUSETTS, ASSIGNOR, BY MESNE ASSIGNMENTS, TO THE RUSSELL COMPANY, A CORPORATION OF MASSACHUSETTS.

MACHINE FOR INTRODUCING KNICKERS INTO FABRICS.

14,724. Specification of Reissued Letters Patent. Reissued Sept. 16, 1919.

Original No. 1,235,327, dated July 31, 1917, Serial No. 90,121, filed April 10, 1916. Application for reissue filed July 16, 1919. Serial No. 311,379.

*To all whom it may concern:*

Be it known that I, WILLIAM S. KINSLEY, of Reading, in the county of Middlesex and State of Massachusetts, have invented certain new and useful Improvements in Machines for Introducing Knickers Into Fabrics, of which the following is a specification.

This invention relates to the manufacture of fabric for clothing which is commonly known as "knickerbocker material" in which spots or nubs of contrasting material appear scattered throughout the fabric.

The most common method of introducing nubs or knickers to the machinery employed in preparing the fibrous material to be spun, is to mix the nubs with the raw or main stock of wool or other material in the picker room, and supply the entire mass of mixed material to the first breaker of a set of carding machines. In other words the nubs were usually mixed with the stock prior to any carding operation. An objectionable result of this operation is that the nubs of fibers become separated or carded to a greater or lesser extent while passing through the carding machines, and if, in order to avoid such result, the workers are raised so high as to avoid objectionable action on the nubs, many of the nubs are liable to drop out and it is impossible to get the best carding results on the rest of the fibers because of such raising of the workers.

Attempts have been made to introduce the nubs or knickers directly to the carding machines, but without really successful results so far as I am aware.

The object of this invention is to obtain the best final results with practically no carding out of the nubs so that they are preserved in their substantially round or pill-like form until the drawing or roving is finally spun.

To attain this result I introduce the nubs at a point intermediate the condition of the material as raw stock in the first card and the point where it issues from the third card as roving ready to be spun. The point of introduction which I prefer is where the main body of the stock or raw stock issues from the second breaker of a set of cards in the form of what is known as "side drawing." The main stock, while in the condition of side drawing, is very loose and fluffy and yet the fibers are sufficiently assembled to not have the general form of the drawing disturbed by the introduction of the nubs, which introduction I preferably accomplish by blowing the nubs into the drawing, the nubs being, of course, in highly scattered relative positions.

By introducing the nubs in the manner described their round or pill-like form is but slightly disturbed or altered when the stock passes through the third breaker and the nubs therefore become carded out to the very least extent, so that instead of some finally appearing in the fabric as short stripes, all really appear as they should, viz., as isolated spots. With the former method, supposing the raw or main stock is white and the knickers are red or blue, the final woven fabric frequently has a reddish or bluish tinge due to the carded out condition of the knickers. By my improvement such fabric retains its white appearance with distinct spots of red or blue.

Of the accompanying drawings in which I have illustrated one embodiment of mechanism including my improvements:—

Fig. 4 represents a section looking down from the line 4—4 in Fig. 1.

Fig. 6 is a detail view looking from the line 6—6 in Fig. 4.

The frame of the machine comprises a suitable base 12, two lower side frame members 13, the two upper side frame members 14, the upper portions of the latter supporting the walls of a distributing chamber 15.

Figure 5:
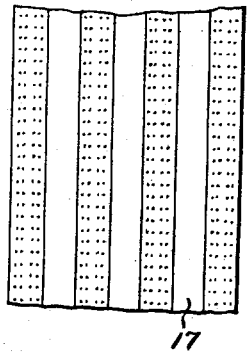
Fig. 5 is a detail elevation of a portion of the conveyer or apron.

The space or chamber which forms the main hopper into which a quantity of the nubs will be deposited, has one wall consisting of a toothed traveling conveyer or apron 17, which preferably has the hook-shaped pins arranged in spaced rows as indicated in Fig. 5, to avoid having too many of the nubs carried up by the apron. I have demonstrated that the arrangement of the hooks or pins in rows as described, better facilitates the elevation of the proper number of nubs, than to have the pins extending over the entire area of the apron, even if the pins were more widely spaced than illustrated.

The belt or apron 17, is mounted on rolls or drums, 18, 19, carried by shafts 20, 21, a support backing 22, being preferably employed to prevent deflection of the rising stretch of the apron out of its proper plane of movement.

Figure 1:
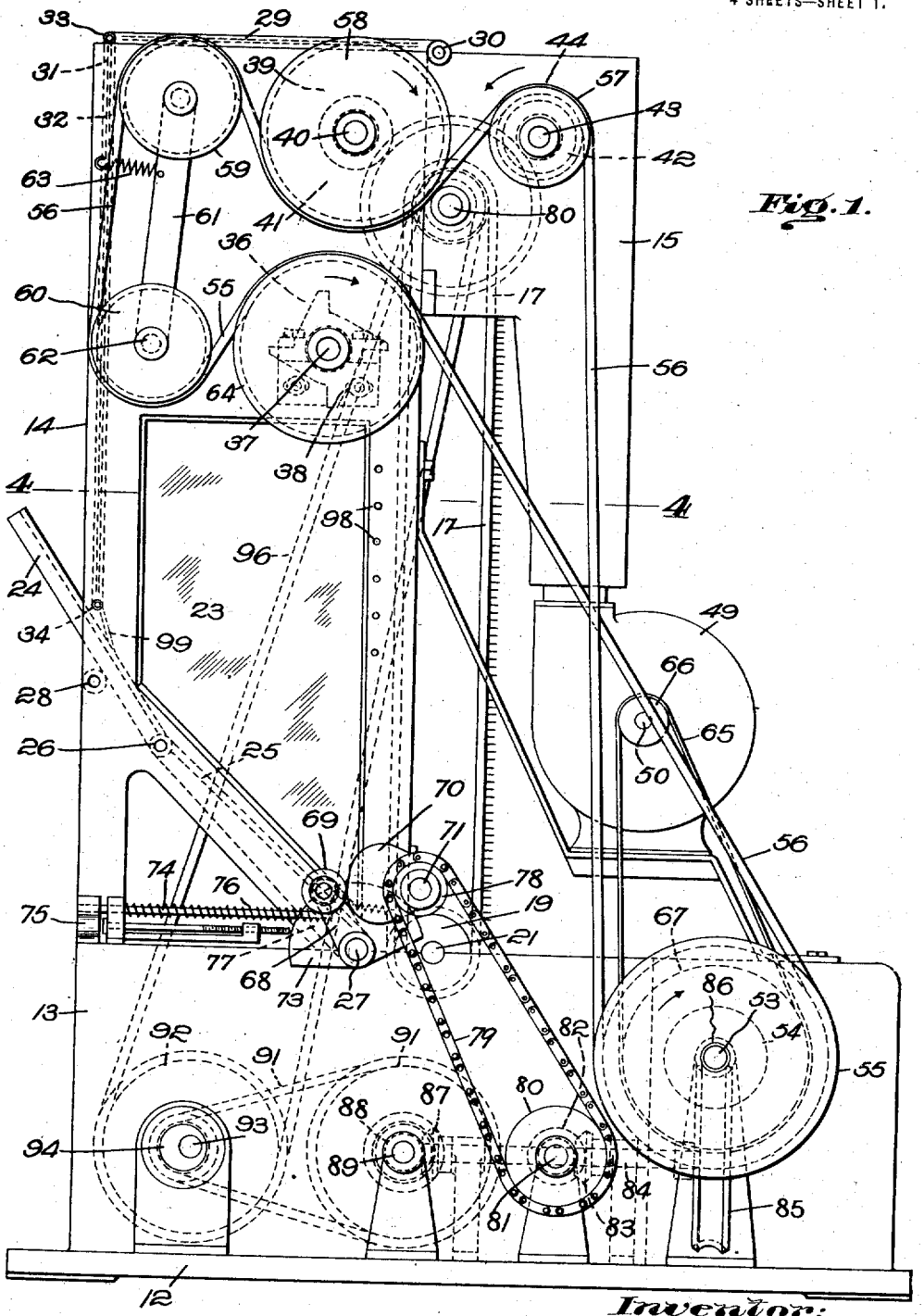
Figure 1 is a side elevation of the machine.

To facilitate an inspection of the stock in the main hopper and to render it possible to observe if the machine is operating properly, I preferably provide the side frame members 14, with transparent glass panels 23. (Figs. 1 and 4).

The bottom of the main hopper constitutes a feeder and comprises two members 24, 25, hinged together at 26, the member 25 being carried by a rock-shaft 27, while the member 24, is free to ride over a roll 28, when the members 24, 25, vibrate from the full line to the dotted line position of Fig. 3, or the reverse, the object of which operation will be hereinafter explained.

A top or cover member 29, is pivoted at 30, so that it can be elevated. A wall or closure for the upper portion of the main hopper, above the member 24, consists of a frame 31, preferably having a glass panel 32, said frame being pivotally connected at 33 to the cover member 29. The lower edge of the frame 31, is provided with small rolls 34 (Fig. 4) entering grooves 35 (see also Fig. 3) formed in the inner faces of the side frame members 14, so that, when the cover is elevated, the frame 31 will also be elevated sufficiently to enable a stock of nubs to be deposited in the hopper through the space thus opened between the lower edge of the raised frame 31, and the bottom member 24. A flexible apron 31[a] depends from the lower edge of the frame 31.

Through driving means and connections hereinafter described the conveyer or apron 17, travels in the direction of the arrow in Fig. 3, the hook pins thereof separating a number of nubs from the stock in the main hopper. To prevent the complete elevation of an excessive number of nubs, I provide a rotary doctor 36, carried by a shaft 37, the latter being mounted in bearings 38, which are preferably horizontally adjustable as indicated in Fig. 1 so that accuracy of operation of the doctor may be effected according to the quality and condition of the stock of nubs operated upon.

Above the doctor 36, is a supplemental doctor comprising a roll 39, carried by a shaft 40, and having straight pins or wires 41, this doctor rotating in the same direction as the doctor 36, and serving to remove from the apron any excess of nubs that might have escaped removal by the doctor 36.

A clearer 42, carried by a shaft 43 and having straight pins or wires 44, revolves in a direction to remove from the teeth or pins of the apron all of those nubs, which have reached a point within the radius of action of said clearer, so as to throw the nubs into the chamber 15, which I refer to as a distributing chamber because when the nubs have reached said chamber they are entirely separate from each other and scattered in a manner that might be compared with snow flakes.

Figure 2:
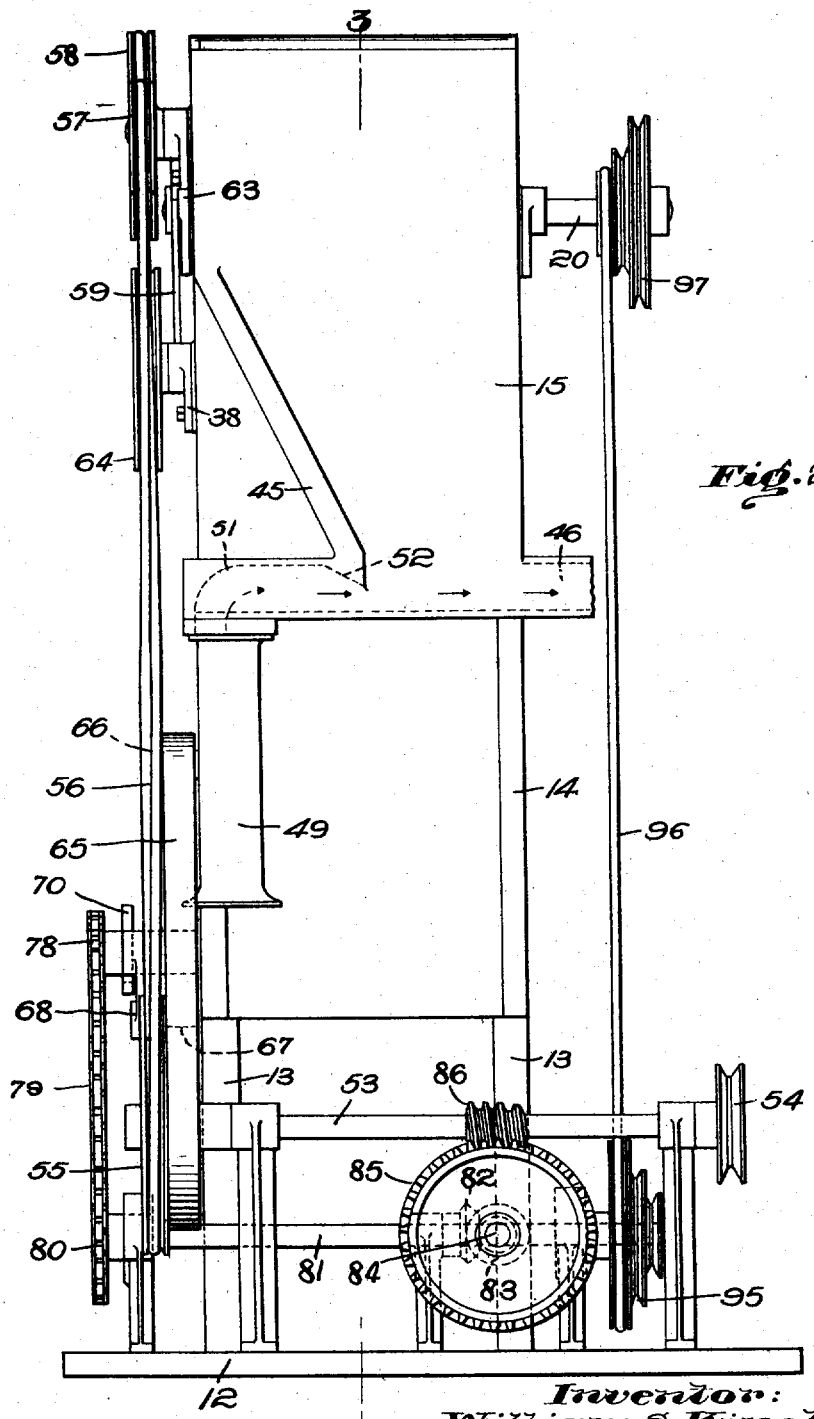
Fig. 2 is an elevation looking from the right of Fig. 1.

One side of the lower portion of the chamber 15, is inclined as best illustrated in Fig. 2, to reduce the area of the outlet from said chamber. From one side of the outlet from this chamber, a tube or passageway 46, extends the required distance and in the proper direction to a somewhat trough-shaped member 47, (see Figs. 4 and 6). This member 47, is located in proper position to support the side drawing *a* as it leaves the usual doffer roll 48, into which drawing *a* the nubs are blown by a current of air supplied by a suitable fan indicated at 49, said fan being carried by a shaft 50. The air outlet from the fan casing enters the box 51 (Fig. 2) and the outlet from said box is directed across the bottom of the distributing chamber 15 and toward the tube or passageway 46. I find in practice that it is advantageous to somewhat reduce or flatten out the current of air sweeping across the bottom of the distributing chamber, and to this end the upper surface of the passage where the air escapes from box 51, is inclined downwardly as shown at 52. It is to be understood at this point that there is never any accumulation of nubs in the bottom of chamber 15. As rapidly as the nubs fall to the bottom of the chamber 15, or nearly reach said bottom, they are taken up by the current of air while still in widely separated or scattered relative positions, and blown through the passageway 46, into the loose side drawing *a*, which is prevented from being deflected out of its usual course by the support 47.

The incline or air deflector 52 causes the air that is forced through by the fan to act upon the air and nubs in chamber 15 somewhat as an ejector to create a suction and facilitate the travel of the scattered nubs through passageway 46.

The main drive shaft 53 having a drive pulley 54 at one end, carries a belt pulley 55 at its other end (Figs. 1 and 2). A belt 56 extends nearly around the pulley 55, and also engages a pulley 57 on the shaft 43, a pulley 58 on the shaft 40, two pulleys 59 and 60, and a pulley 64 on the shaft 37. The pulleys 59, 60 are practically idle pulleys, the pulley 59 being carried by an arm or arms 61 pivotally supported on the axis 62 of the pulley 60, and having a suitably connected spring 63, to enable the pulley 59 to act as a belt tightener.

A belt 65, to operate the fan connects a pulley 66 carried by the fan shaft 50, with a pulley 67 on the main drive shaft 53. I will now describe the means for vibrating or oscillating the hopper bottom members 24, 26, so as to keep the stock of nubs subject to intermittent and yielding pressure or impulses toward the conveyer or apron to feed the nubs to the apron: Mounted loosely on shaft 27 (Figs. 1 and 4), is an arm 68 carrying a roll 69, which is acted on by a cam 70, carried by a shaft 71. A segment 72 is rigidly carried by rock-shaft 27, and has a stop block 73 for the arm 68 to contact with. A rod 74 pivotally connected to the segment extends through a guide bracket 75, a spring 76 coiled upon the rod acting, through the segment and its block 73, to cause the feed member 25 to act yieldingly, on the stock of nubs when pressing them toward the apron. The guide bracket 75 is adjustable to vary the force of said spring to vary the number of nubs taken up by the apron. The greater the pressure, the more nubs will be taken up.

A spring 77 connects the arm 68 with the segment so that the roll 69 of the arm will keep in constant contact with the cam.

Figure 3:
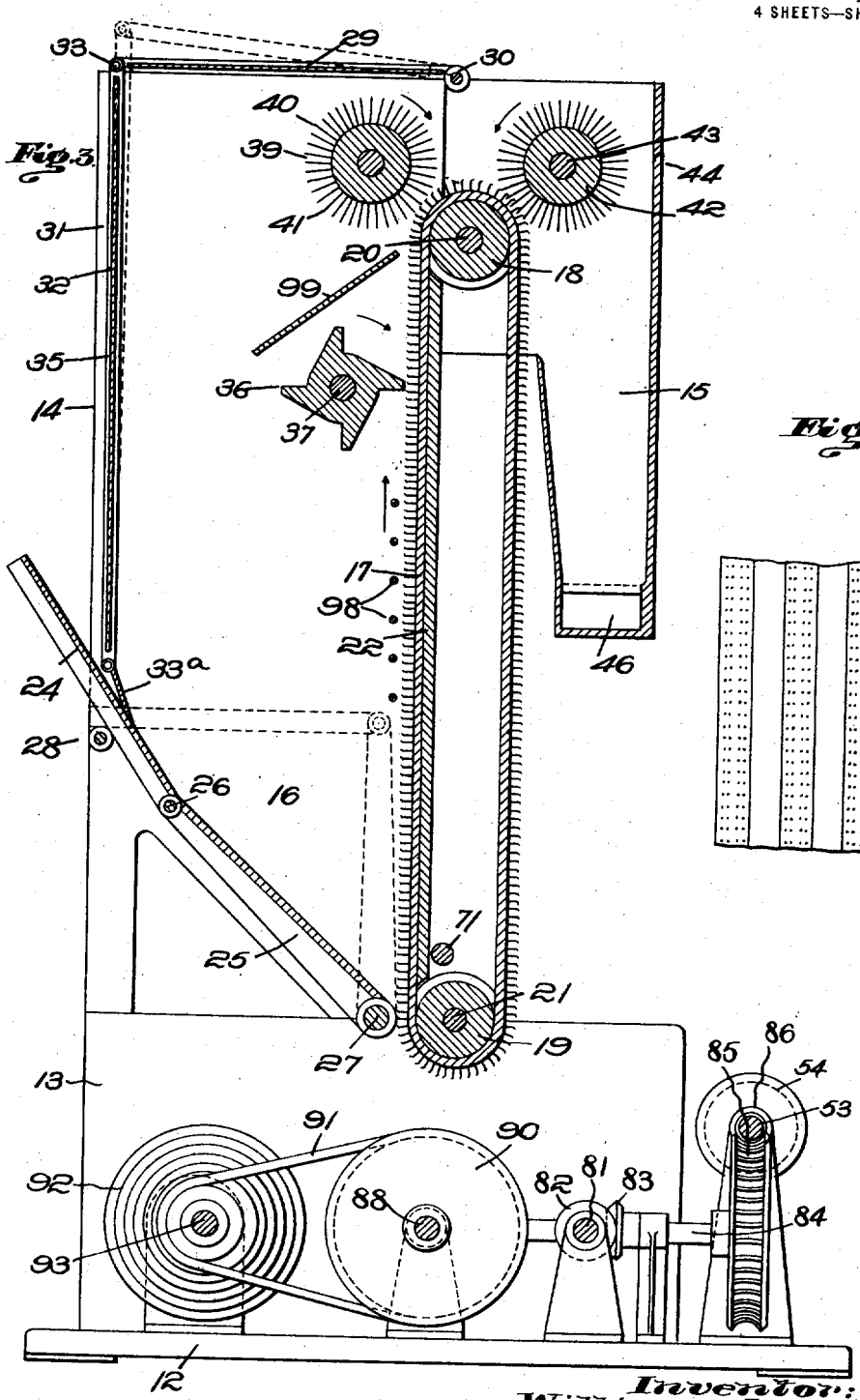
Fig. 3 represents a section on line 3—3 of Fig. 2.

As the feed board member 24 shifts, as indicated by the full and dotted lines in Fig. 3, there would necessarily be an open space at times between the frame 31, through which nubs would escape when the main hopper is filled above that level. The apron 31[a] prevents such escape, and at the same time yields to permit the member 24 to shift.

A sprocket 78 carried by shaft 71, is connected by a chain 79, with a sprocket 80, carried by a shaft 81 (Figs. 1 and 4) said shaft 81 having a bevel pinion 82 meshing with a bevel pinion 83, carried by a shaft 84, having a worm-wheel 85 which is engaged with and actuated by a worm 86, carried by the main drive shaft 53. From this it will be understood that the rotation of the cam 70, is quite slow, said cam serving to shift the bottom members 24, 25, to substantially the full line position of Fig. 3, after which the spring 76 serves to yieldingly carry the bottom members toward the dotted line position of said figure. So long as there is considerable stock in the main hopper 16, the bottom members cannot of course reach the dotted line position referred to, but the member 25, will even then act through the stock to keep intermittently pressing the stock of nubs toward the conveyer or apron. As the amount of stock decreases, the very last of it will be taken up by the conveyer or apron because, as the amount of stock gradually decreases to almost nothing, any nubs that are on the member 24, will slide therefrom onto the member 25, when said members are in the full-line position of Fig. 3 and will then be pressed up to position to be taken by the hook pins of the apron.

As is well-known, the drawing or roving issuing from a set of cards is caused to vary in size and speed of travel, in order to produce different sizes of yarn to be woven. It is of course desirable to vary the number of knickers or nubs delivered by my machine through the passageway 46, so that the yarn or the final fabric will have the proper, or any desired, percentage of knickers. One way to vary the said percentage as illustrated in Figs. 1, 2 and 4, is to vary the speed of travel of the apron.

The shaft 84 has a bevel pinion 87 (see Figs. 1, 2, 4) meshing with a bevel pinion 88, carried by a shaft 89, carrying a cone step pulley 90, which is connected by a shiftable belt 91, with a cone step pulley, 92, carried by a shaft 93 mounted in adjustable eccentric bearings 94. The shaft 93 has step pulleys 95 connected by a belt 96, with step pulleys 97 carried by the upper shaft 20 for the conveyer or apron. By adjusting the belts 91 and 96, relatively to the step pulleys on which said belts run, the speed of travel of the apron may be varied without, of course, affecting in any way the speed of operation of the other moving parts.

Practically the bottom members 24, 25 of the main hopper constitute a feed board mechanism which enables the feed to take care of itself. This is because the point to which the member 25 moves toward the conveyer or apron depends upon the amount of stock between the member 25 and the apron, and the amount of pressing force imparted by the spring 76.

A series of transverse rods 98, supported by the side frame members 14, and adjacent to the tips of the pins of the apron, serve to prevent any of the stock of nubs that are above the plane of action of the feeder from interfering with the operation of the apron or with the nubs that have been taken from the supply at the lower part of the hopper 16. Without a guard such as provided by the rods 98, it would be difficult to properly control the quantity of nubs carried up, because there might be a greater surplus elevated than could be removed by the doctor mechanism.

To prevent the nubs which are removed by the upper doctor 39, from falling onto the lower doctor and back on the apron, a deflector 99 is employed to direct the removed and falling nubs behind the doctor 36.

By my improved method it is not necessary to employ as large a percentage of nubs in order to obtain the desired results in the fabric, and owing to the fact that the number of processes to which the nubs are subjected is reduced, the liability of their dropping out is lessened. And since the nubs are not materially carded out, they look larger in the finished product.

Of course it will be understood, without detailed description that the drawing *a* after the introduction of the nubs thereinto, is afterward converted into roving to be spun or twisted into yarn for the manufacture of woven knickerbocker material.

As indicated in Fig. 4 by the breaking of the passageway or conduit 46 said conduit may be of any length. And it will be readily understood that more than one of my improved machines may be connected to said conduit. If several are connected, and their hoppers are supplied with nubs or knickers of different qualities or colors, then a variation of the nubs delivered at the end of the conduit may be quickly effected by simply selecting for operation those machines which contain the nubs that may be needed for the desired combination of colors or qualities.

By the employment of the terms "side drawing" or "roving" herein, I do not limit myself to the definition employed by any one authority, because the authorities are not in accord in their definitions on this subject. According to some, the term "sliver" would better define the condition of the main stock as it leaves the doffer 48 as hereinbefore described, but in many woolen mills the term "roving" or "side drawing" is employed, and I prefer to employ these terms although with no intention of limiting myself thereby, because I believe myself to be the first to introduce nubs of one kind of fibrous material into material of another kind by blowing one into the other while said other is traveling, regardless of whether said other material be slightly twisted or not, and called "sliver", "roving" or "drawing". Of course it is essential, for successful operation, that said other material be in sufficiently loose and fluffy condition to permit the nubs to be blown into it enough to cause the nubs to be then carried along for the further treatment including final spinning.

Having now described my invention in one of its embodiments without attempting to disclose all possible modifications thereof, what I claim is:

1. The combination with a carding machine, of an independent receptacle for fibrous material of a different nature from the material of the main stock treated in the machine, a conduit connecting the said machine and independent receptacle, and means for blowing the material through said conduit.

2. The combination with mechanism for producing side drawing of fibrous material to be spun, of means for introducing nubs into said drawing by means of currents of air after said material is formed as drawing.

3. A machine of the character described comprising a support for a fibrous roving or drawing, a receptacle for fibrous material, a chamber having an outlet delivering at one side of said support, means for continuously transferring small quantities of the material from the receptacle to said chamber, and means for directing a current of air toward and through the chamber outlet.

4. A machine of the character described comprising a support for a fibrous roving or drawing, a receptacle for fibrous material, a chamber having an outlet delivering at one side of said support, means for continuously transferring small quantities of the material from the receptacle to said chamber, said means consisting of an elevating toothed apron and a clearer for removing the material from the apron and scattering it into the chamber, and means for directing a current of air toward and through the chamber outlet.

5. A machine of the character described, comprising a support for a fibrous roving or drawing, and means for blowing scattered fibrous material of a different nature from the material of the roving or drawing into said roving or drawing while the latter is on said support.

6. A machine of the character described, comprising a support for a fibrous roving or drawing, said support being open at both ends, a tube connecting with the support intermediate its ends, and means for blowing fibrous material of a different nature from the material of the drawing through said tube into the drawing.

7. A machine of the character described, comprising a receptacle for fibrous material, an elevating apron in said receptacle, a feeder for insuring the constant supply of material to the apron, a chamber for receiving material elevated by the apron, and means for blowing the material from said chamber into a roving or drawing, the said fibrous material being of a different nature from the material of the roving or drawing.

8. A machine of the character described, comprising a receptacle for fibrous material, an elevating apron in said receptacle, a vibratory feeder for insuring the constant supply of material to the apron, a chamber for receiving material elevated by the apron, and means for blowing the material from said chamber into a roving or drawing.

9. A machine of the character described, comprising a receptacle for fibrous material, an elevating apron in said receptacle, a feeder for insuring the constant supply of material to the apron, a chamber for receiving material elevated by the apron, and means for blowing the material from said chamber into a roving or drawing, said feeder having a hinged member forming the bottom of the receptacle, means being provided for yieldingly moving the hinged member toward the apron and positively moving it away from the apron.

10. A machine of the character described, comprising a receptacle for fibrous material, an elevating apron in said receptacle, a feeder for insuring the constant supply of material to the apron, a chamber for receiving material elevated by the apron, and means for blowing the material from said chamber into a roving or drawing, said feeder consisting of two supports hinged together, and means for oscillating one of said supports.

11. A machine of the character described, comprising a receptacle for fibrous material, an elevating apron in said receptacle said apron having pins in spaced rows, a chamber for receiving material elevated by the apron, and means for blowing the material from said chamber into a roving or drawing.

12. A machine of the character described, comprising a receptacle for fibrous material, a toothed apron in said receptacle, a chamber for receiving material elevated by the apron, means for blowing the material from said chamber into a roving or drawing, and means for prescribing the amount of material delivered by the apron into said chamber.

13. A machine of the character described, comprising a receptacle for fibrous material, a toothed apron in said receptacle, a chamber for receiving material elevated by the apron, means for blowing the material from said chamber into a roving or drawing, and adjustable doctor mechanism for prescribing the amount of material delivered by the apron into said chamber.

14. A machine of the character described, comprising a receptacle for fibrous material, an elevating apron in said receptacle, a feeder for insuring supply of material to the lower part of the apron, guard devices for preventing material in the upper part of the receptacle from engaging the apron, a chamber for receiving material elevated by the apron, and means for delivering material from said chamber to a roving or drawing.

15. The method of introducing nubs of one kind of fibrous material into fibrous material of another kind for the production of knickerbocker goods, consisting in causing the last mentioned material to travel, and blowing the nubs into the last mentioned material while it is traveling.

16. The method of preparing the fibrous material for the production of knickerbocker woven goods, consisting in producing roving, blowing nubs into said roving, and supporting the roving against the pressure of the current of air.

17. In a machine of the character described, carding mechanism including a doffer and means for feeding knickers of supplementary stock to the roving of regular stock after such regular stock has been removed from the doffer.

18. In a machine of the character described, carding mechanism including a doffer and means for feeding knickers of supplementary stock to the roving of regular stock after such regular stock has been removed from the doffer and before the formation of the roving is complete.

19. In a machine of the character described, carding mechanism including a doffer and means for feeding knickers of supplementary stock to the roving of regular stock after such regular stock has been removed from the doffer and before the formation of the roving is complete, thereby to inclose said knickers in the cross-roving of regular stock.

20. The method of introducing nubs of one kind of fibrous material into fibrous material of another kind for the production of knickerbocker goods which comprises causing the last mentioned material to travel in a roving and introducing the nubs into the roving while it is traveling.

21. The method of introducing nubs of one kind of fibrous material into fibrous material of another kind for the production of knickerbocker goods which comprises starting the formation of a traveling roving of the last mentioned material and introducing the nubs into the traveling roving prior to the completion thereof, thereby to inclose the nubs in the completed roving.

22. The combination with a carding machine of a chamber having an outlet presented adjacent the surface of the doffer roll, means for depositing knickers in the chamber and means for creating an air current in the chamber to disseminate the knickers therein and deliver them in disseminated condition to the carded material.

In testimony whereof I have affixed my signature.

WILLIAM S. KINSLEY.

Copies of this patent may be obtained for five cents each, by addressing the "Commissioner of Patents, Washington, D. C."